United States Patent [19]

Gillessen et al.

[11] 4,276,049

[45] Jun. 30, 1981

[54] METHOD FOR THE DETERMINATION OF AN AMINO OR AMINOSULPHONIC ACID

[75] Inventors: Dieter Gillessen, Pratteln; William Lergier, Kaiseraugst, both of Switzerland

[73] Assignee: Hoffmann-La Roche Inc., Nutley, N.J.

[21] Appl. No.: 92,315

[22] Filed: Nov. 8, 1979

[30] Foreign Application Priority Data

Nov. 10, 1978 [CH] Switzerland ............... 11589/78

[51] Int. Cl.³ ............................................. G01N 33/68
[52] U.S. Cl. ................................... 23/230 B; 23/903
[58] Field of Search ................. 23/230 R, 230 B, 903

[56] References Cited

U.S. PATENT DOCUMENTS

| 3,745,212 | 7/1973 | Benneville et al. | 23/903 X |
|---|---|---|---|
| 3,871,825 | 3/1975 | Leimburger et al. | 23/903 X |
| 3,892,530 | 7/1975 | Felix et al. | 23/230 R |
| 3,933,430 | 1/1976 | Hare | 23/230 R |
| 3,969,373 | 7/1976 | Cleeland, Jr. et al. | 260/347.3 |

FOREIGN PATENT DOCUMENTS 2134850 12/1972 France .

OTHER PUBLICATIONS

Reeder et al., Chem. Abstr. 89 (1978), 19514e.
Benson et al., Chem. Abstr. 82 (1975), 149032n.

*Primary Examiner*—Arnold Turk
*Attorney, Agent, or Firm*—Jon S. Saxe; Bernard S. Leon; James H. Callwood

[57] ABSTRACT

Method for the determination of an amino benzoic acid or aminosulphonic acid in urine, plasma or serum. The method consists essentially in reacting a urine, plasma or serum sample with a compound of the 4-phenylspiro[furan-2(3H)1'-phthalan]-3,3'-dione type or with a compound of the 2-methoxy-2,4-diphenyl-3(2H)-furanone type or with o-phthaldialdehyde and subsequently carrying out a photometric measurement.

8 Claims, No Drawings

METHOD FOR THE DETERMINATION OF AN AMINO OR AMINOSULPHONIC ACID

BACKGROUND OF THE INVENTION

The present disclosure relates to the assaying of an aromatic amino or aminosulphonic acid of the general formula

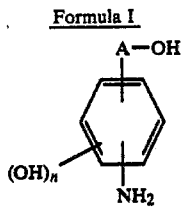

Formula I wherein A is CO or $SO_2$ and n equals 0, 1 or 2 in a urine, plasma or serum sample to determine the proper functioning of the pancreas.

Certain peptides which contain an amino or aminosulphonic acid group of the general formula

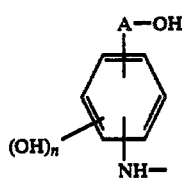

Formula I' wherein A and n have the significance given earlier, are used as diagnostic agents for the determination of the pancreas function. An especially suitable peptide for this purpose is N-benzoyl-L-tyrosyl-p-aminobenzoic acid of the formula

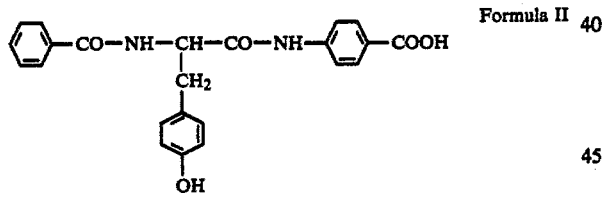

Formula II

In principle, assays to determine pancreas function are carried out as follows:

A sufficient amount of a suitable peptide containing an amino or aminosulphonic acid group of formula I' is administered to a fasted trial person from whom any previous medicaments, especially sulphonamides, sulphonylurea compounds and pancreas enzymes, have been withdrawn. A sufficient diuresis is provided for by permitting water to be drunk. The peptide which has been administered is cleaved by the chymotrypsin produced by the pancreas, a large part of the amino or aminosulphonic acid of formula I being excreted in the urine as such or in metabolized form. In order to recover any metabolized amino or aminosulphonic acids of formula I, the urine is conveniently hydroylzed prior to the determination. Depending on the percentage amount of amino or aminosulphonic acid of formula I found in the urine sample, the function of the pancreas can be elucidated. When N-benzoyl-L-tyrosyl-p-aminobenzoic acid is used as the peptide, p-aminobenzoic acid is determined in the urine sample as the amino acid of formula I. The determination of the amino or aminosulphonic acid of formula I can, however, also be carried out using plasma or serum.

In the known determination method according to Bratton and Marshall, the amino or aminosulphonic acid of formula I present in the urine sample is diazotized and coupled to a coloring substance, which is then determined colorimetrically. Since this determination method is relatively costly, there exists a need for a simpler and less complicated determination method.

DETAILED DESCRIPTION OF THE INVENTION

In accordance with the present invention, it has now been found that the amino or aminosulphonic acid of formula I present in the urine or in the albumin-free plasma or serum can be determined by reaction thereof with a 4-phenyl-spiro[furan2(3H)1'-phthalan]-3,3'-dione type compound of the formula

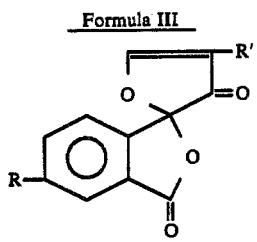

Formula III wherein R is hydrogen, halogen, lower alkyl or lower alkoxy and R' is lower alkyl or aryl or with a 2-methoxy-2,4-diphenyl-3(2H)-furanone type compound of the formula

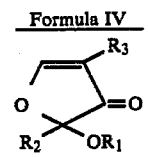

Formula IV wherein $R_1$ is lower alkyl, phenyl lower alkyl; $R_2$ is phenyl or substituted phenyl; and $R_3$ is substituted or unsubstituted phenyl, naphthyl or indolyl, or with o-phthaldialdehyde under strong acid conditions (pH ca 1.5-3) and in the presence of an inert organic solvent and subjecting the complex obtained to a photometric measurement.

Preferred compounds of formula III are those wherein R is hydrogen. Examples of preferred compounds are:
4 phenylspiro[furan-2(3H),1'-phthalan] 3,3'-dione
4-(2-methoxyphenyl)spiro[furan-2(3H),1'-phthalan]-3,3'-dione
4-(3-methoxyphenyl)spiro[furan-2(3H),1'-phthalan]-3,3'-dione
4-(4-methoxyphenyl)spiro[furan-2(3H),1'-phthalan]-3,3'-dione
4-(2,4-dimethoxyphenyl)spiro[furan-2(3H),1'-phthalan]-3,3'-dione
4-(2,5-dimethoxyphenyl)spiro[furan-2(3H),1'-phthalan]-3,3'-dione
4-(3,5-dimethoxyphenyl)spiro[furan-2(3H),1'-phthalan]-3,3'-dione
4-(3,4,5-trimethoxyphenyl)spiro[furan-2(3H),1'-phthalan]-3,3'-dione 4-(2,4,5-trimethoxyphenyl)spiro[furan-2(3H)-1'-phthalan]-3,3'-dione
4-(3,4-methylenedioxyphenyl)spiro[furan-2(3H),1'-phthalan]-3,3'-dione
4-(3-chlorophenyl)spiro[furan-2(3H),1'-phthalan]-3,3'-dione
4-(4-chlorophenyl)spiro[furan-2(3H),1'-phthalan]-3,3'-dione
4-(4-bromophenyl)spiro[furan-2(3H),1'-phthalan]-3,3'-dione
4-(3-indolyl)spiro[furan-2(3H),1'-phthalan]-3,3'-dione
4-(2-naphthyl)spiro[furan-2(3H),1'-phthalan]-3,3'-dione
4-(1-naphthyl)spiro[furan-2(3H),1'-phthalan]-3,3'-dione
4-(1-propyl)spiro[furan-2(3H),1'-phthalan]-3,3'-dione.

Especially preferred is the compound wherein R' is phenyl, i.e., 4-phenylspiro[furan-2(3H),1'-phthalan]-3,3'-dione.

Preferred compounds of formula IV are those wherein $R_1$ is lower alkyl, $R_2$ is phenyl and $R_3$ is phenyl or phenyl substituted by carboxy or carboxy lower alkyl. Particularly preferred compounds of formula I are the compounds wherein $R_1$ is methyl and $R_2$ and $R_3$ are phenyl, i.e., 2-methoxy-2,4-diphenyl-3(2H)furanone, $R_1$ is methyl, $R_2$ is phenyl and $R_3$ is 4-carboxyphenyl, i.e., 2-methoxy-2-phenyl-4-(4-carboxyphenyl)-3(2H)furanone and $R_1$ is methyl, $R_2$ is phenyl and $R_3$ is 4-(2-carboxyethyl)phenyl, i.e., 2-methoxy-2-phenyl-4-[4-(2-carboxyethyl)phenyl]-3(2H)furanone.

The present invention is based on the foregoing finding and is accordingly concerned with a method for the determination of an amino or aminosulphonic acid of formula I in urine, plasma or serum, which method comprises reacting a urine sample, which may be diluted with water, or an albumin-free plasma or serum sample under strong acid conditions and in the presence of an inert organic solvent with a compound of formula III or with a compound of formula IV or with o-phthaldialdehyde and subsequently carrying out a photometric measurement.

4-Phenyl-spiro[furan-2(3H)1'-phthalan]-3,3'-dione as well as compounds of this type are known from U.S. Pat. Nos. 3,812,181, 3,871,825, 3,917,646 and 3,957,826. 2-Methoxy-2,4-diphenyl-3(2H)-furanone as well as compounds of this type are known from U.S. Pat. Nos. 3,969,373, 4,018,884, 4,038,289 and 4,045,487.

A preferred embodiment of the present invention consists in using 4-phenyl-spiro[furan-2(3H)1'-phthalan]-3,3'-dione, 2-methoxy-2,4-diphenyl-3(2H)-furanone or o-phthaldialdehyde as the reagent, the first-named compound being especially preferred. When 4-phenyl-spiro[furan-2(3H)1'-phthalan]-3,3'-dione is used, the reaction is carried out in the presence of an inert organic solvent. In accordance with this invention, any conventional inert organic solvent can be utilized. Acetone or ethanol is preferred as the solvent. Also, when 2-methoxy-2,4-diphenyl-3(2H)-furanone is used, the reaction is carried out in the presence of an inert organic solvent. In accordance with this invention, any conventional inert organic solvent can be utilized. When o-phthaldialdehyde is used, ethanol is preferably used as the solvent and mercaptoethanol as the reduction agent. The optimum pH range for the reaction lies at ca 2–2.5. This is achieved by diluting, with water or buffering, the urine sample which is too acid after the hydrolysis. A sodium acetate buffer or a potassium chloride/hydrochloric acid buffer is preferably used as the buffer.

The following examples illustrate the present invention:

EXAMPLE 1

(a) Determination Method 1 ml of undiluted urine and 0.1 ml of 10 N hydrochloric acid were heated in a closed test tube for 1 hour at 96° ±2° C. in a water-bath.

0.1 ml of the hydrolyzed urine, 5 ml of sodium acetate buffer and 1 ml of Fluram ® reagent were mixed well and left to stand for 15 minutes. After 15 minutes, analytical samples were removed, and the extinctions were measured at 400 nm (405 nm with filters) against a control (measurement batch as above, but containing 0.1 ml of water in place of hydrolyzed urine).

(b) Preparation of the Sodium Acetate Buffer 27.21 g of sodium acetate trihydrate were dissolved in ca 500–700 ml of bidistilled water, and the pH was then adjusted to 3 while stirring and adding glacial acetic acid dropwise. After adding 3 drops of pHix preserving agent, the volume was made up to 1000 ml with water. There was obtained a 0.2 M sodium acetate buffer of pH 3. In place of this buffer, there can also be used the buffer prepared as follows:

2.72 g of sodium acetate were dissolved in ca 900 ml of bidistilled water, and the pH was then adjusted to 3 by adding ca 55 ml of glacial acetic acid. The solution was diluted with water to a volume of 1000 ml, and there was obtained a 0.02 M sodium acetate buffer.

(c) Preparation of Fluram ® Reagent 140 mg of 4-phenyl-spiro[furan-2(3H)1'-phthalan]-3,3'-dione (Fluram ®) was dissolved in 1000 ml of acetone.

Production of a Standard Curve

(a) Stock Solution

Ca 40 mg of p-aminobenzoic acid was dissolved in 30 ml of acetone, and the solution was made up to a volume of 100 ml with sodium acetate buffer.

(b) Dilutions

Ca 8 μg/0.1 ml = 2 ml of stock solution + 8 ml of sodium acetate buffer

Ca 16 μg/0.1 ml = 4 ml of stock solution + 6 ml of sodium acetate buffer

Ca 20 μg/0.1 ml = 5 ml of stock solution + 5 ml of sodium acetate buffer

Ca 24 μg/0.1 ml = 6 ml of stock solution + 4 ml of sodium acetate buffer

Ca 32 μg/0.1 ml = 8 ml of stock solution + 2 ml of sodium acetate buffer

Ca 40 μg/0.1 ml = undiluted

The extinctions were measured at 400 nm (405 nm with filters) analogously to the urine samples, and the measured values are marked on millimeter paper. A linear standard curve was obtained.

EXAMPLE 2

Determination Method

The procedure described in Example 1 was repeated using 2-methoxy-2,4-diphenyl-3(2H)-furanone in place of 4-phenyl-spiro[furan-2(3H)1'-phthalan]-3,3'-dione. The extinctions were measured at 320 nm.

Standard Curve

There was obtained a linear standard curve in the range of 40–200 μg of paminobenzoic acid per measurement batch (ca 3–6 ml).

EXAMPLE 3

Determination Method

The precedure described in Example 1 was repeated using o-phthaldialdehyde in ethanol containing 0.5% mercaptoethanol in place of Fluram® reagent. The extinctions were measured at 420 nm.

Standard Curve

There was obtained a linear standard curve in the range of 8–80 μg of p-aminobenzoic acid per measurement batch (ca 3–6 ml).

EXAMPLE 4

The procedure described in Example 1 was repeated using 1 ml of albumin-free plasma or serum. The de-albumination can be carried out according to methods known per se. There was obtained a linear standard curve in the range of 2–35 μg of p-aminobenzoic acid per measurement batch as in Example 1.

What is claimed is:

1. A method for the determination of an amino or aminosulphonic acid of the general formula

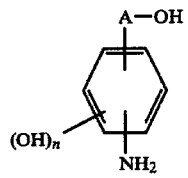

wherein A is CO or $SO_2$ and n equals 0, 1 or 2 in urine, plasma or serum, which method comprises reacting a urine sample or an albumin-free plasma or serum sample under strong acidic conditions with a reagent selected from the group consisting essentially of a compound of the formula

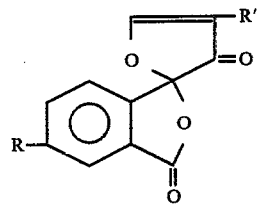

wherein R is hydrogen, halogen, lower alkyl or lower alkoxy and R' is lower alkyl or aryl; and a compound of the formula

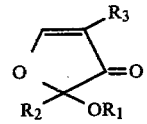

wherein $R_1$ is lower alkyl, phenyl lower alkyl; $R_2$ is phenyl or substituted phenyl; and $R_3$ is substituted or unsubstituted phenyl, naphthyl or indolyl, and o-phthaldialdehyde; and subsequently carrying out a photometric measurement.

2. A method according to claim 1 wherein said urine, plasma or serum sample is hydrolyzed prior to said determination.

3. A method according to claim 2 wherein 4-phenyl-spiro[furan-2(3H)1'-phthalan]-3,3'-dione is used as said reagent, and said reaction is carried out in the presence of an inert solvent and in a pH range of ca 2–2.5.

4. A method according to claim 3 wherein acetone is used as said inert organic solvent.

5. A method according to claim 3 wherein ethanol is used as said solvent.

6. A method according to claim 5 wherein the reaction is carried out in a buffer system.

7. A method according to claim 6 wherein sodium acetate is used as said buffer.

8. A method according to claim 6 wherein potassium chloride/hydrochloric acid is used as said buffer.

* * * * *